United States Patent [19]

Nelson

[11] Patent Number: 6,149,933
[45] Date of Patent: Nov. 21, 2000

[54] DIETARY SUPPLEMENT FOR PROMOTION OF HEALTHY HAIR AND PIGMENT RESTORATION

[75] Inventor: Julia A. Nelson, Fort Worth, Tex.

[73] Assignee: Summa Rx Laboratories, Inc., Mineral Wells, Tex.

[21] Appl. No.: 09/111,563

[22] Filed: Jul. 8, 1998

Related U.S. Application Data

[60] Provisional application No. 60/052,179, Jul. 10, 1997.
[51] Int. Cl.$^7$ ............... A61K 9/28; A61K 9/68; A61K 39/385; A61K 7/06; A61K 7/04
[52] U.S. Cl. ............ 424/441; 424/61; 424/70.1; 424/74; 424/195.1; 424/440; 426/599; 514/846; 514/847
[58] Field of Search ............... 424/441, 440, 424/61, 70.1, 74, 195.1; 426/599; 514/846, 847

[56] References Cited

U.S. PATENT DOCUMENTS

| | | | |
|---|---|---|---|
| 5,529,769 | 6/1996 | Cho et al. | 424/74 |
| 5,744,187 | 4/1998 | Gaynor | 426/599 |
| 5,846,569 | 12/1998 | Anderson et al. | 424/535 |

OTHER PUBLICATIONS

Naturue's Herbs Power Herbs Supplement—Cat's Claw Powder, Product Alert, AN 96:109536 PROMT Abstract, Feb. 1996.
Forbes, Micronutrient status inpatients receiving home parenteral nutrition; AN 1998011959 EMBASE abstract, 1997.
Tyrosinase Inhibition Due to Interaction of Homocyst(eine with Copper: The Mechanism for Reversible Hypopigmentation in Homocystinuria Due to Cystathionine Beta–Synthase Deficiency, Dept. of Pediatrics, University of Minnesota, American Journal of Humal Arnet., Reish et al., 1995
Science News, vol. 151, Jan. 11, 1997, p. 26, ". . .gray hair from smoking . . .".
Olivares and Uauy, "Deficiency of Copper in Humans", pp. 792S–796S, (Jan. 1997).
Journal of the A.M.A., Sep. 27, 1941, "Queries and Minor Notes", Restoration of Hair Color, pp. 1140–1141.
Reish et al., "Tyrosinase Inhibition Due to Interaction of Homocyte (e) ine with Copper: The Mechanism for Reversible Hypopigmentation in Homocystinuria Due to Cystathionine β–Synthase Deficiency", Am. J. Hum. Genet., 57:127–132, 1995.
Novelli, David G., "Metabolic Functions of Pantothenic Acid", vol. 33, Oct. 1953, 525–543.
Menkes et al., "A Sez–Linked Recessive Disorder With Retardation of Growth, Peculiar Hair, and Focal Cerebral and Cerebellar Degeneration", Pediatrics, May 1962, pp. 764–779.
Stop the Age Robbers, pp. 179–182, "Hair Loss—Rethinking Your True Colors." (1980).
Stop the Age Robbers, pp. 183–188, "Hair Loss—Winning over Thinning", (1980).
"Water–Soluble Vitamins", Recommended Dietary Allowances, 10th Edition, Food and Nutrition Board, National Academy Press 1989, pp. 115–124.
"Water–Soluble Vitamins", Ascorbic Acid, Ascorbic Acid (Vitamin C), pp. 1525, 1547–1550, (1989).
"Water–Soluble Vitamins", Hematopoietic Agents: Growth Factors, Minerals, and Vitamins, "Copper", pp. 1292–1293, 1527, (1989).
"Water–Soluble Vitamins", Pyridoxine, pp. 1538–1540, (1989).
Brody, Nutritional Biochemistry, "Zinc and Copper", pp. 581–592, (1980).
Collie, William R, et al., Hair in Menkes Disease: A Comprehensive Review, pp. 198–209, (1979).
Shoen, Linda Allen, et al., "Hair: Facts and Basic Care", The Look You Like, pp. 1–9, (1990).
Kobori, Tatsuji et al., Biology and Disease of the Hair, Tokyo, Japan, Oct. 6–9, 1975, Proceedings of the First International Symposium on Biology and Disease of Hair.
Robbins, Clarence R., Chemical and Physical Behavior of Human Hair, Third Edition, (1994).

Primary Examiner—Kimberly Jordan
Attorney, Agent, or Firm—Fitch, Even, Tabin & Flannery

[57] ABSTRACT

A dietary supplement which is useful for the promotion of healthy hair and pigment restoration in human subjects is provided. The dietary supplement supplies useful nutrients for hair growth, development, and pigmentation. In some instances, the use of the present dietary supplement can retard, prevent, suppress, and/or even reverse the graying of hair. Thus, at least for some already-turned gray individuals, the natural hair color can be restored, and maintained, naturally without the use of dyes, colorants, or the like. The dietary supplement contains, in effective amounts, a copper salt; para-aminobenzoic acid or salts thereof; pantothenic acid or salts thereof; and vitamin B6 in an appropriate carrier.

22 Claims, No Drawings

DIETARY SUPPLEMENT FOR PROMOTION OF HEALTHY HAIR AND PIGMENT RESTORATION

This application claims the benefit of U.S. Provisional Application No. 60/052,179, filed Jul. 10, 1997.

FIELD OF THE INVENTION

This invention generally relates to a dietary supplement which is useful for the promotion of healthy hair and pigment restoration in human subjects. The dietary supplement of the present invention supplies useful nutrients for hair growth, development, and pigmentation. In some instances, the use of the present dietary supplement can retard, prevent, suppress, and/or even reverse the graying of hair. Thus, at least for some already-turned gray individuals, the natural hair color can be restored, and maintained, naturally without the use of dyes, colorants, or the like. And, at least for some not-yet turned gray individuals, the natural hair color can be maintained for longer periods (and perhaps indefinitely) than would have otherwise been the case.

BACKGROUND OF THE INVENTION

Human hair is the keratin-containing threadlike outgrowths extending from hair follicles in the skin. In humans, hair generally serves protective, sensory, and sexual attractiveness functions. A mature hair shaft is composed of three, and sometimes four, basic structures. The cuticle is the thick outer protective covering consisting of flat overlapping scalelike layers. The cortex is located inside, and is surrounded by, the cuticle. The cortex contains fibrous proteins which are aligned along the length of the hair axis. Thicker hairs often contain one or more porous regions—the medulla—located near or at the center of the hair shaft. The fourth basic component is the intercellular cement which glues or binds the cells together and provides the main pathway for diffusion into the hair fibers. Melanocytes which produce melanin, the pigment responsible for hair color, are generally contained in the cortex and the base of the bulb of the hair shaft. Essential nutrients and oxygen are carried to the growing hair through capillaries around the base of the bulb.

Gray hair, like death and taxes, is often considered to be inevitable part of life and the aging process. Graying of hair generally results from a gradual replacement of pigmented hair by unpigmented hair as the melanocytes shut down pigment production as one gets older. This graying process often starts at around age forty (although it can begin much earlier or later) with the onset and rate of graying apparently controlled mainly by genetics. By some estimates, approximately 50 percent of all women will be at least partially gray by the age of fifty. In most cases, the graying process has generally been considered irreversible; once the hair follicle starts to produce gray hair, it is not likely to change back. Thus, for most individuals with graying or already-turned gray hair the options are limited: acceptance of the situation or masking with colorants, bleaches, dyes, highlights, head coverings, or wigs. Once coloring techniques are used, however, they must be repeated (or at least touched up) on a regular basis to maintain the color and avoid undesirable gray roots.

It would be desirable, therefore, to provide alternatives for combating gray hair, especially ones which will increase and promote the overall healthiness of the hair. It would also be desirable to provide a method by which, at least in some cases, the onset of gray hair can be significantly delayed or even prevented. It would also be desirable to provide a method by which, at least in some cases, already-turned gray hair can be restored to its original natural color. The dietary supplement and methods of the present invention provides such benefits and advantages.

SUMMARY OF THE INVENTION

This invention generally relates to a dietary supplement which is useful for the promotion of healthy hair and pigment restoration in human subjects. More specifically, this invention relates to a dietary supplement which, with regular use, promotes and maintains healthy hair growth and pigmentation. The dietary supplement of the present invention supplies useful nutrients for hair growth, development, and pigmentation. In some instances, the use of the present dietary supplement can retard, prevent, suppress, and/or even reverse the graying of hair. Thus, at least for some already-turned gray individuals, the natural hair color can be restored, and maintained, naturally without the use of dyes, colorants, or the like. Likewise, individuals who have not turned gray or have just begun the graying process may be able, in some instances, to maintain, and perhaps even enhance, their natural hair color without the use of dyes, colorants, or the like. The dietary supplement of the present invention contains, in effective dosage or amounts, a copper salt; para-aminobenzoic acid or salts thereof; pantothenic acid or salts thereof; and vitamin B6, all of which are contained in an appropriate carrier. The dietary supplement of this invention is designed to be taken on a regular basis (e.g., one to four times daily) for the promotion and maintenance of healthy human hair.

One object of the present invention is to provide a dietary supplement for promoting healthy hair, said dietary supplement comprising, in effective dosage, a copper salt; para-aminobenzoic acid or salts thereof; pantothenic acid or salts thereof; and vitamin B6 in a carrier, wherein said dietary supplement, when administered to a human on a regular basis, is effective in promoting and maintaining healthy hair.

Another object of the present invention is to provide a method for promoting healthy hair in a human, said method comprising administering a dietary supplement to the human on a regular basis, wherein the dietary supplement contains, in effective dosage, a copper salt; para-aminobenzoic acid or salts thereof; pantothenic acid or salts thereof; and vitamin B6 in a carrier, wherein said dietary supplement is effective in promoting and maintaining healthy hair.

These and other objects and advantages of the present invention will be apparent from a consideration of the present specification.

DETAILED DESCRIPTION OF THE INVENTION

The present invention relates to a dietary supplement that is useful in promoting and maintaining healthy hair and, in some cases, is useful in retarding, preventing, suppressing, and/or even reversing the graying of hair. The dietary supplement of the present invention supplies useful nutrients for hair growth, development, and pigmentation. Thus, at least for some already-turned gray individuals, the natural hair color can be restored, and maintained, naturally without the use of dyes, colorants, or the like. Likewise, individuals who have not turned gray or have just begun the graying process may be able, in some instances, to maintain, and perhaps even enhance, their natural hair color without the use of dyes, colorants, or the like. The dietary supplement of the present invention contains, in effective amounts, a copper salt; para-aminobenzoic acid or salts thereof; pantothenic acid or salts thereof; and vitamin B6, all of which are contained in an appropriate carrier. The dietary supplement of this invention is designed to be taken on a regular basis (e.g., one to four times daily) for the promotion and maintenance of healthy human hair.

The dietary supplement of this invention contains a copper salt; para-aminobenzoic acid or salts thereof; pantothenic acid or salts thereof; and vitamin B6 in an appropriate carrier. Copper, generally in the form of a water soluble or slightly water soluble salt, can be present as either copper (I) or copper (II) ions. Generally, the copper salt is preferably in the copper (II) form. Examples of suitable copper salts include, for example, copper gluconate, cupric chloride, cupric sulfate, cupric carbonate, cupric glycinate, cupric hydroxide, cupric oxide, cuprous iodide, cuproxoline, and the like. Generally, the preferred copper salts are copper gluconate and cupric sulfate. Generally, the copper salt is present at a level of greater than about 1.0 mg Cu/day. Preferably, the copper salt is present at a level of about 1.0 to about 10 mg Cu/day; more preferably, the copper salt is present at about 3 to about 7 mg Cu/day. For purposes of this invention, dosages, unless specified otherwise, are given in total quantity per day. Thus, for a dosage of about 1.0 mg Cu/day, a single tablet containing 1.0 mg Cu, two tablets each containing about 0.5 mg Cu, three tablets each containing about 0.33 mg Cu, or the like taken during a 24 hour period could be used to supply the desired dosage.

The dietary supplement of this invention also contains various B-complex vitamins including para-aminobenzoic acid or salts thereof; pantothenic acid or salts thereof; and vitamin B6. Generally, para-aminobenzoic acid or salts thereof are present at a level of greater than about 75 mg/day. Preferably, para-aminobenzoic acid or salts thereof are present at a level of about 100 to about 700 mg/day; more preferably, at about 300 to about 500 mg/day. Suitable para-aminobenzoic acid salts include, for example, the diethylamine salt of para-aminobenzoic acid, the potassium salt of para-aminobenzoic acid, and the like. Generally, pantothenic acid (Vitamin B5) or salts thereof are present at a level of greater than about 10 mg/day. Preferably, pantothenic acid or salts thereof are present at a level of about 100 to about 1500 mg/day; more preferably, at about 750 to about 1000 mg/day. Suitable pantothenic acid salts include, for example, calcium pantothenate, sodium pantothenate, and the like. Generally, vitamin B6 is present at a level of greater than about 2.0 mg/day. Preferably, vitamin B6 is present at a level of about 2.5 to about 5.0 mg/day. Vitamin B6 can be present in any form, including, for example, pyridoxine, pyridoxal, pyridoxamine, pyridoxal-5-phosphate, pyridoxine dihydrochloride, and the like. If desired, other B-complex vitamins, such as inositol, niacin, and niacinamide, may also be included.

The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or non-coated), tea, or the like. The dietary supplement is preferably in the form of a tablet or capsule and most preferably in the form of a hard gelatin capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. Preferably, the dietary supplement is administered orally one to two times daily. Frequency of administration will, of course, depend on the dose per unit (capsule or tablet) and the desired level of ingestion. Dose levels/unit can be adjusted to provide the recommended levels of ingredients per day in a reasonable number of units (e.g., two capsules or tablets taken twice a day).

The dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: asorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

The dietary supplement of this invention contains a copper salt; para-aminobenzoic acid or salts thereof; pantothenic acid or salts thereof; and vitamin B6 in an appropriate carrier. Preferably, the dietary supplement of this invention also contains ascorbates (generally greater than about 50 mg/day), silica (generally greater than about 5 mg/day), Fo-Ti (generally greater than about 2 mg/day), Cat's Claw (generally greater than about 2 mg/day), and nettles (generally greater than about 2 mg/day). Especially preferred dietary supplements are described in the examples below.

Use of the dietary supplement of this invention on a regular basis (e.g., daily) can promote and encourage healthy hair, especially scalp hair. For some individuals, the use of this dietary supplement can retard, prevent, suppress, and/or even reverse the graying of hair. Thus, at least for some already-turned gray individuals, the natural hair color can be restored, and maintained, naturally without the use of dyes, colorants, or the like. It is estimated that about 20 to 50 percent of gray-haired individuals will be able to at least partially restore their natural hair color using the present dietary supplement on a regular basis.

Since the exposed hair is composed of dead cells, the visible effects of the dietary supplement will generally require new growth of the hair to occur. This process may, therefore, take several months to be noticed over the entire scalp depending on the rate of growth for a given individual. Once a more natural hair color has been restored, the dosage of the dietary supplement or the frequency of use can, if desired, be reduced while still maintaining the desired effects. Nonetheless, it is generally preferred that daily use at the same dosage levels be continued for maximum benefit. Although not wishing to be limited by theory, it is believed that the dietary supplement provides and supplies the needed nutrients, vitamins, minerals, and other like to the hair, including the melanocytes, to stimulate healthy hair growth and pigmentation. The use of a vasodilator—such as Minoxidil applied topically for the treatment of baldness—can apparently increase the supply of blood to the area around the hair follicle. The use of the present dietary supplement and a vasodilator such as Minoxidil are expected, therefore, to increase the effectiveness of each as compared to use of either alone.

The following examples are intended to illustrate, but not to limit, the invention.

EXAMPLE 1

A dietary supplement containing the following ingredients was prepared in a tablet form using maltodextrin, calcium carbonate, and magnesium stearate as carriers. Each tablet weighed about 721 mg.

|  | Tablet (mg) | Daily Dosage (mg) |
| --- | --- | --- |
| Copper gluconate | 5.8 | 23.1 |
| Para-aminobenzoic acid | 125.0 | 500 |
| Calcium pantothenate | 273.0 | 1091.8 |
| Fo-Ti | 12.5 | 50.0 |
| Bioflavinoids | 5.0 | 20.0 |
| Calcium ascorbate | 31.3 | 125.0 |
| Cat's Claw | 1.0 | 4.0 |
| Pyridoxine HCl | 1.3 | 5.0 |
| Nettles | 5.0 | 20.0 |
| Silica | 2.5 | 10.0 |
| Kelp | 2.5 | 10.0 |
| Horsetail | 1.0 | 4.0 |
| Rosemary | 1.0 | 4.0 |
| Dulse | 1.0 | 4.0 |
| Spirulina | 1.0 | 4.0 |
| Maltodextrin | 100.0 | 400.0 |
| Calcium carbonate | 150.0 | 600.0 |
| Magnesium stearate | 2.5 | 10.0 |

Standard dosage is two tablets taken orally twice a day.

EXAMPLE 2

A dietary supplement containing the following ingredients could be prepared in a capsule form using maltodextrin and magnesium stearate as carriers. Each capsule would weigh about 485 mg (net).

|  | Capsule (mg) | Daily Dosage (mg) |
| --- | --- | --- |
| Copper gluconate | 5.8 | 23.1 |
| Para-aminobenzoic acid | 125 | 500 |
| Calcium pantothenate | 273 | 1092 |
| Fo-Ti | 12.5 | 50 |
| Bioflavinoids | 5 | 20 |
| Calcium ascorbate | 31.3 | 125 |
| Cat's Claw | 1 | 4 |
| Pyridoxine HCl | 1.3 | 5 |
| Nettles | 5 | 20 |
| Silica | 2.5 | 10 |
| Kelp | 2.5 | 10 |
| Horsetail | 1 | 4 |
| Rosemary | 1 | 4 |
| Dulse | 1 | 4 |
| Spirulina | 1 | 4 |
| Maltodextrin | 13.5 | 54 |
| Magnesium stearate | 2.5 | 10 |

Standard dosage would be two capsules taken orally twice a day.

EXAMPLE 3

A dietary supplement containing the following ingredients could be prepared in a tablet form. Each tablet would weigh about 1200 mg.

|  | Tablet (mg) | Daily Dosage (mg) |
| --- | --- | --- |
| Copper gluconate | 15.4 | 30.8 |
| Para-aminobenzoic acid | 200 | 400 |
| Calcium pantothenate | 218.4 | 437 |
| Fo-Ti | 25 | 50 |
| Ascorbic Acid | 100 | 200 |
| Cat's Claw extract (4:1) | 5 | 10 |
| Pyridoxine HCl | 10 | 20 |
| Nettles | 2 | 4 |
| Silica | 5 | 10 |
| Microcrystalline cellulose | 100 | 200 |
| Stearic Acid | 15 | 30 |
| Dicalcium phosphate | 475 | 950 |
| Sodium Starch Glycolate | 6 | 12 |

Standard dosage would be one tablet taken orally twice a day.

EXAMPLE 4

A dietary supplement containing the following ingredients could be prepared in a capsule form. Each capsule would weigh about 500 mg (net).

|  | Capsule (mg) | Daily Dosage (mg) |
| --- | --- | --- |
| Copper gluconate | 11.5 | 11.5 |
| Para-aminobenzoic acid | 200 | 200 |
| Calcium pantothenate | 273 | 273 |
| Pyridoxine HCl | 2.5 | 2.5 |
| Magnesium stearate | 5 | 5 |

Standard dosage would be one tablet or capsule taken daily.

EXAMPLE 5

A dietary supplement containing the following ingredients could be prepared in a tablet form. Each tablet would weigh about 1000 mg.

|  | Tablet (mg) | Daily Dosage (mg) |
| --- | --- | --- |
| Copper gluconate | 11.5 | 11.5 |
| Para-aminobenzoic acid | 200 | 200 |
| Calcium pantothenate | 328 | 328 |
| Pyridoxine HCl | 5 | 5 |
| Magnesium stearate | 10 | 10 |
| Dicalcium phosphate | 451 | 451 |
| Sodium Starch Glycolate | 5 | 5 |

Standard dosage would be one tablet taken daily.

EXAMPLE 6

A dietary supplement containing the following ingredients could be prepared in a tablet form. Each tablet would weigh about 1000 mg.

|  | Tablet (mg) | Daily Dosage (mg) |
| --- | --- | --- |
| Copper gluconate | 12.8 | 38.4 |
| Para-aminobenzoic acid | 150 | 450 |
| Calcium pantothenate | 273 | 819 |
| Fo-Ti | 8.3 | 25 |

-continued

|  | Tablet (mg) | Daily Dosage (mg) |
| --- | --- | --- |
| Bioflavinoids | 3.3 | 10 |
| Calcium ascorbate | 10.4 | 31.2 |
| Rose hips | 3.3 | 10 |
| Ascorbic Acid | 10 | 30 |
| Acerola | 5 | 15 |
| Cat's Claw extract (4:1) | 3.3 | 10 |
| Pyridoxine HCl | 1 | 3 |
| Pyridoxyl-5-phosphate | 0.7 | 2 |
| Nettles | 3.3 | 10 |
| Silica | 6.7 | 20 |
| Horsetail | 1.7 | 5 |
| Rosemary | 1.7 | 5 |
| Dulse | 1.7 | 5 |
| Spirulina | 1.7 | 5 |
| Inositol | 1.7 | 5 |
| Niacin | 3.3 | 10 |
| DHEA | 8.3 | 25 |
| Green Tea | 3.3 | 10 |
| Selenium aspartate | 8.3 | 25 |
| Zinc oxide | 5 | 15 |
| Magnesium stearate | 8.3 | 25 |
| Calcium carbonate | 450 | 1350 |

Standard dosage would be three tablets taken daily.

In the above Examples, the dosages could be increased or decreased for individual cases. It is generally preferred that the standard dosage be maintained until the desired results are obtained (often within about two months). Thereafter, the standard or even a reduced dosage could be used for maintenance purposes as needed in individual cases.

The formulations of this invention, included the formulation included in these Examples, could be formed as coated tablets or capsules or other forms that may be more acceptable to the consumer. Additionally, the total and/or relative amounts of the various ingredients could be increased or decreased per tablet or capsule to allow the consumer to take more or fewer tablets or capsule per day.

EXAMPLE 7

A number of volunteers have taken the dietary supplement (using the formulation essentially as described in Example 1) for varying lengths of time in order to evaluate its effectiveness. The following results, which are based on qualitative data reported by the volunteers, were obtained.

Subject No. 1 (61 year old male non-smoker) took the dietary supplement for approximately one year. At the beginning of the trial, the subject's hair was mostly dark brown with the typical salt and pepper effect beginning to be noticeable. Throughout the study, the progression of graying was essentially halted with some return of the natural hair color noted. Overall hair health was improved in that thicker and shinier hair was noted.

Subject No. 2 (35 year old male non-smoker) took the dietary supplement sporadically for about two to four weeks. The subject's hair at the beginning of the trial was prematurely gray with only a small percentage of the natural hair coloring remaining. The subject reported that friends indicated that his hair was much darker after use of the dietary supplement.

Subject No. 3 (35 year old female smoker) took the dietary supplement for about four weeks. The subject's hair at the beginning of the trial was long with a prematurely gray streak. After only two weeks, the gray streak had dramatically diminished. The subject found the results to be very striking.

Subject No. 4 (49 year old female smoker) took the dietary supplement for about two weeks on a fairly regular basis. The subject's hair at the beginning of the trial was completely white. After only two weeks, some darker hair was visible at the temples.

Subject No. 5 (39 year old female smoker) took the dietary supplement for only two weeks. No visible changes were reported.

Subject No. 6 (44 year old male non-smoker) took the dietary supplement for only two weeks. No visible changes were reported.

Subject No. 7 (61 year old male non-smoker) took the dietary supplement for about eight months on a regular basis. At the beginning of the study, the subject's hair was a salt and pepper mix with about 20 to 30 percent gray. At the end of the eight months treatment, the subject's spouse reported that graying had been halted and that, perhaps, the hair was a little darker. No other effects were reported.

Subject No. 8 (58 year old male non-smoker) took the dietary supplement for about five months on a regular basis. At the beginning of the study, the subject was balding with an overall salt and pepper effect. At the end of the five months treatment period, the subject's spouse reported that the overall health of his hair had improved and that there was a gradual restoration of the natural color.

Subject No. 9 (58 year old female non-smoker) took the dietary supplement for a period of about eighteen months with good results. At the beginning of the study, the subject's hair was mostly dark brown with the beginning of an overall salt and pepper effect. During the course of the treatment, progression of graying was halted and some regression of graying was noted. Hair health was also reported to be improved. At one point during the study, the subjected discontinued use of the supplement for about two months. During this two month period, a much more rapid progression of gray was noted. Resuming treatment resulted in a reversal of the graying noted in the two month period when treatment had stopped.

That which is claimed is:

1. A dietary supplement for promoting healthy hair, said dietary supplement comprising, in effective dosage, a copper salt; para-aminobenzoic acid or salts thereof; pantothenic acid or salts thereof; and vitamin B6 in a carrier, wherein said dietary supplement, when administered to a human on a regular basis, is effective in promoting and maintaining healthy hair.

2. A dietary supplement as defined in claim 1, wherein the dosage of the copper salt is greater than about 1.0 mg Cu/day, the dosage of the para-aminobenzoic acid or salts thereof is greater than about 75 mg/day, the dosage of the pantothenic acid or salts thereof is greater than about 10 mg/day, and the dosage of the vitamin B6 is greater than about 2.0 mg/day.

3. A dietary supplement as defined in claim 2, wherein the dosage of the copper salt is about 1.0 to about 10 mg Cu/day, the dosage of the para-aminobenzoic acid or salts thereof is about 100 to about 700 mg/day, the dosage of the pantothenic acid or salts thereof is about 100 to about 1500 mg/day, and the dosage of the vitamin B6 is about 2.5 to about 5.0 mg/day.

4. A dietary supplement as defined in claim 2, further comprising ascorbates, silica, Fo-Ti, Cat's Claw, and nettles.

5. A dietary supplement as defined in claim 4, wherein the dosage of ascorbates is greater than about 50 mg/day, the dosage of silica is greater than about 5 mg/day, the dosage of Fo-Ti is greater than about 2 mg/day, the dosage of Cat's Claw is greater than about 2 mg/day, and the dosage of nettles is greater than about 2 mg/day.

6. A dietary supplement as defined in claim 1, wherein the copper salt is copper (II) gluconate or copper (II) sulfate; the para-aminobenzoic acid or salts thereof are para-aminobenzoic acid, diethylamine salt of para-aminobenzoic acid, or potassium salt of para-aminobenzoic acid; the pantothenic acid or salts thereof are pantothenic acid, calcium pantothenate, or sodium pantothenate; and the vitamin B6 is in the form of pyridoxine, pyridoxal, pyridoxamine, pyridoxal-5-phosphate, or pyridoxine dihydrochloride.

7. A dietary supplement as defined in claim 3, wherein the copper salt is copper (II) gluconate or copper (II) sulfate; the para-aminobenzoic acid or salts thereof are para-aminobenzoic acid, diethylamine salt of para-aminobenzoic acid, or potassium salt of para-aminobenzoic acid; the pantothenic acid or salts thereof are pantothenic acid, calcium pantothenate, or sodium pantothenate; and the vitamin B6 is in the form of pyridoxine, pyridoxal, pyridoxamine, pyridoxal-5-phosphate, or pyridoxine dihydrochloride.

8. A dietary supplement as defined in claim 1, wherein the dietary supplement is in the form of a capsule or tablet and the carrier is selected from the group consisting of calcium carbonate, magnesium stearate, maltodextrin, and mixtures thereof.

9. A method for promoting healthy hair in a human, said method comprising administering a dietary supplement to the human on a regular basis, wherein the dietary supplement contains, in effective dosage, a copper salt; para-aminobenzoic acid or salts thereof; pantothenic acid or salts thereof; and vitamin B6 in a carrier, wherein said dietary supplement is effective in promoting and maintaining healthy hair.

10. A method as defined in claim 9, wherein the dosage of the copper salt is greater than about 1.0 mg Cu/day, the dosage of the para-aminobenzoic acid or salts thereof is greater than about 75 mg/day, the dosage of the pantothenic acid or salts thereof is greater than about 10 mg/day, and the dosage of the vitamin B6 is greater than about 2.0 mg/day.

11. A method as defined in claim 10, wherein the dosage of the copper salt is about 1.0 to about 10 mg Cu/day, the dosage of the para-aminobenzoic acid or salts thereof is about 100 to about 700 mg/day, the dosage of the pantothenic acid or salts thereof is about 100 to about 1500 mg/day, and the dosage of the vitamin B6 is about 2.5 to about 5 mg/day.

12. A method as defined in claim 10, wherein the dietary supplement further comprises, in effective dosage, ascorbates, silica, Fo-Ti, Cat's Claw, and nettles.

13. A method as defined in claim 12, wherein the dosage of ascorbates is greater than about 50 mg/day, the dosage of silica is greater than about 5 mg/day, the dosage of Fo-Ti is greater than about 2 mg/day, the dosage of Cat's Claw is greater than about 2 mg/day, and the dosage of nettles is greater than about 2 mg/day.

14. A method as defined in claim 9, wherein the copper salt is copper (II) gluconate or copper (II) sulfate; the para-aminobenzoic acid or salts thereof are para-aminobenzoic acid, diethylamine salt of para-aminobenzoic acid, or potassium salt of para-aminobenzoic acid; the pantothenic acid or salts thereof are pantothenic acid, calcium pantothenate, or sodium pantothenate; and the vitamin B6 is in the form of pyridoxine, pyridoxal, pyridoxamine, pyridoxal-5-phosphate, or pyridoxine dihydrochloride.

15. A method as defined in claim 11, wherein the copper salt is copper (II) gluconate or copper (II) sulfate; the para-aminobenzoic acid or salts thereof are para-aminobenzoic acid, diethylamine salt of para-aminobenzoic acid, or potassium salt of para-aminobenzoic acid; the pantothenic acid or salts thereof are pantothenic acid, calcium pantothenate, or sodium pantothenate; and the vitamin B6 is in the form of pyridoxine, pyridoxal, pyridoxamine, pyridoxal-5-phosphate, or pyridoxine dihydrochloride.

16. A method as defined in claim 9, wherein the dietary supplement is in the form of a capsule or tablet and the carrier is selected from the group consisting of calcium carbonate, magnesium stearate, maltodextrin, and mixtures thereof.

17. A method as defined in claim 9, further comprising applying a vasodilator to the scalp.

18. A method as defined in claim 15, further comprising applying a vasodilator to the scalp.

19. A method as defined in claim 17, wherein the vasodilator is Minoxidil.

20. A method as defined in claim 18, wherein the vasodilator is Minoxidil.

21. A method as defined in claim 9, wherein the method is also effective in retarding, preventing, suppressing, or reversing graying of hair.

22. A method as defined in claim 10, wherein the method is also effective in retarding, preventing, suppressing, or reversing graying of hair.

* * * * *